(12) United States Patent
Ulrich

(10) Patent No.: US 9,283,128 B2
(45) Date of Patent: Mar. 15, 2016

(54) COTTON PAD DISPENSER AND A METHOD FOR ITS PRODUCTION

(75) Inventor: Hans Ulrich, Holbæk (DK)

(73) Assignee: EAZY-PAC DANMARK A/S, Holbaek (DK)

( * ) Notice: Subject to any disclaimer, the term of this patent is extended or adjusted under 35 U.S.C. 154(b) by 207 days.

(21) Appl. No.: 13/821,510

(22) PCT Filed: Sep. 9, 2011

(86) PCT No.: PCT/DK2011/050335
§ 371 (c)(1),
(2), (4) Date: Jul. 9, 2013

(87) PCT Pub. No.: WO2012/031600
PCT Pub. Date: Mar. 15, 2012

(65) Prior Publication Data
US 2013/0277387 A1    Oct. 24, 2013

(30) Foreign Application Priority Data
Sep. 10, 2010   (DK) .................................. 2010 70390

(51) Int. Cl.
*B65D 83/08* (2006.01)
*A61F 15/00* (2006.01)

(52) U.S. Cl.
CPC .......... *A61F 15/001* (2013.01); *B65D 83/0847* (2013.01)

(58) Field of Classification Search
CPC ......... A61F 15/001; A47F 1/08; A47F 1/082; B65D 71/36; B65D 5/725; B65D 5/726; B65D 5/727; B65D 83/04; B65D 83/0847
USPC ....................................................... 221/309
See application file for complete search history.

(56) References Cited

U.S. PATENT DOCUMENTS

| 1,890,295 | A |   | 12/1932 | Jacobs |
| 2,115,923 | A |   | 5/1938  | Cooper |
| 3,450,308 | A | * | 6/1969  | Schoenefeld ................. 221/305 |
| 4,053,242 | A | * | 10/1977 | Mast, Jr. ....................... 221/232 |

(Continued)

FOREIGN PATENT DOCUMENTS

| CA | 1070272 A1 | 1/1980 |
| DE | 4214649 A1 | 11/1993 |

(Continued)

OTHER PUBLICATIONS

International Search Report issued in related PCT patent application PCT/DK2011/050335 dated Nov. 24, 2011, 5 pages.

(Continued)

*Primary Examiner* — Timothy Waggoner
(74) *Attorney, Agent, or Firm* — Lathrop & Gage LLP

(57) ABSTRACT

The cotton pad dispenser (1) comprises a side wall (2) extending between a top and a bottom end of the dispenser (1), and an end wall (7) near the bottom end, a plurality of disc-shaped cotton pads (9) being stacked within the dispenser. A first cut-out (3) provided in said side wall (2) extends upwards from the bottom end of the dispenser (1) so as to form an entrance into said volume through the side wall (2), and a second cut-out (4) provided in said end wall (7) extends from the first cut-out (3) such that the cut-outs (3, 4) comprise a mutual transition to form one combined withdrawal aperture (1a). The withdrawal aperture (1a) is arranged such as to enable withdrawal of a bottommost cotton pad by gripping a peripheral portion (9b) of the cotton pad (9) with an indexing finger and a thumb, and pulling the cotton pad out of the withdrawal aperture (1a) by means of deformation of the cotton pad (9).

18 Claims, 2 Drawing Sheets

(56) References Cited

U.S. PATENT DOCUMENTS

| | | | |
|---|---|---|---|
| 4,101,053 A | | 7/1978 | Mast, Jr. |
| 4,170,325 A | * | 10/1979 | Pawlowski et al. ........... 221/311 |
| 4,253,842 A | * | 3/1981 | Ehrlich ........................ 221/309 |
| 4,538,726 A | * | 9/1985 | Pastva ....................... 221/312 C |
| 5,211,308 A | * | 5/1993 | Decker et al. ................... 221/63 |
| 5,501,365 A | | 3/1996 | Richiger et al. |
| 5,704,714 A | | 1/1998 | Stary |
| 5,713,488 A | * | 2/1998 | Farrugia ........................ 221/45 |
| 5,899,356 A | | 5/1999 | Huisman |
| 6,109,787 A | | 8/2000 | Stary |
| 6,279,776 B1 | * | 8/2001 | Finkletaub et al. ........... 221/281 |
| 6,588,626 B2 | | 7/2003 | Sauer et al. |
| 2002/0130170 A1 | | 9/2002 | Nakashima |
| 2005/0276653 A1 | | 12/2005 | Thiebaut |
| 2009/0302051 A1 | | 12/2009 | Nygaard-Petersen |

FOREIGN PATENT DOCUMENTS

| | | |
|---|---|---|
| DE | 20315697 U1 | 2/2005 |
| DE | 202004000696 U1 | 5/2005 |
| DE | 202006000578 U1 | 3/2006 |
| DE | 202008005811 U1 | 7/2008 |
| EP | 410937 A1 | 1/1991 |
| EP | 1000872 A1 | 5/2000 |
| FR | 1552684 A1 | 1/1969 |
| FR | 2749151 A | 12/1997 |
| GB | 1513660 A | 6/1978 |
| JP | 58107379 A | 6/1983 |
| JP | 63274519 A | 11/1988 |
| JP | 08276938 A | 10/1996 |
| RU | 2123464 C1 | 12/1998 |
| WO | 0001271 A1 | 1/2000 |
| WO | 2008003316 A1 | 1/2008 |
| WO | 2009034323 A2 | 3/2009 |
| WO | 2010074001 A1 | 7/2010 |

OTHER PUBLICATIONS

Translation of Japanese Application No. 2013-527472, Office Action dated Sep. 1, 2015, 4 pages.

* cited by examiner

COTTON PAD DISPENSER AND A METHOD FOR ITS PRODUCTION

BACKGROUND

1. Field of the Invention

The present invention relates in a first, second and third aspect to dispensers for dispensing cotton pads according to the introductory parts of claims 3, 1 and 6, respectively. In a fourth aspect (claim 8) the invention relates to a method for producing a dispenser according to claim 1.

2. Description of the Related Art

The cotton pads to which the present invention relates are of the disc-shaped, typically round type, which are often used to apply or remove make-up, e.g. in bathrooms or beauty parlors. Thus, depending on how the cotton pads are stored they risk being subjected to soil and moisture. Since cotton pads inherently have a very absorbing nature, specifically subjection to moisture often instantly will make the cotton pads unusable. It is therefore desirable to provide a dispenser that protects the cotton pads from moist and soil.

To this end applicant's WO 2008/003316, on which the introductory parts of claims 3, 1 and 6 are based, discloses a cotton pad dispenser within which a number of disc-shaped cotton pads are stacked. The cotton pads are enclosed within a circular-cylindrical side wall, which is closed at the top end and at the bottom of which an end wall is positioned to keep the cotton pads within the dispenser when placed in an upright position. At the bottom end of the dispenser the side wall extends beyond the end wall such as to form a supporting structure for supporting the dispenser in the upright position. The end wall comprises a central, circular withdrawal aperture. The end wall is raised a short distance above the surface onto which the dispenser is positioned, which prevents the bottommost cotton pad of the dispenser from coming into contact with especially moist, but also soil on the surface on which the dispenser is positioned. Even though such an arrangement of an aperture allows for withdrawal of cotton pads one by one, the dispenser must be lifted from the surface in order to withdraw a cotton pad, and preferable tilted in order to see the aperture and then withdraw a cotton pad through it by means of a user's fingers. When the dispenser is no longer entirely full, the cotton pads may during tilting of the dispenser fall from the bottommost position down in the dispenser toward the top end due to the force of gravity, thereby making the bottommost cotton pad inaccessible from the withdrawal aperture. Furthermore, due to the flexible nature of cotton pads, gripping the bottommost cotton pad is difficult since a user's fingers will often push the stack of cotton pads into the dispenser. Also, gripping a cotton pad at the centre portion of its flat surface and pulling it out of the dispenser will often tend to somewhat destroy the fragile structure of this surface, which subsequently is less suitable for example for applying make-up.

SUMMARY

On this background it is the object of the first aspect of the invention to ease withdrawal of a cotton pad from a dispenser of the type described in the introduction.

This object is met with a dispenser according to claim 3.

Provision of a first cut-out in the side wall and a second cut-out in the end wall, such as to create a mutual transition between the two, forms one single combined withdrawal aperture which opens both at the side and at the bottom of the dispenser. Hereby a peripheral portion of the bottommost cotton pad can be gripped with for example an indexing finger of a hand inserted through the second cut-out and a thumb of the hand inserted through the first cut-out. This makes it easier for a user to get a firm grip on the cotton pad since the user will have a finger on each side of the disc-shaped cotton pad instead of two fingers on the same side. Of course, gripping a peripheral portion of the bottommost cotton pad with for example a thumb of a hand, inserted through the second cut-out, and an indexing finger of the hand, inserted through the first cut-out, is also conceivable.

The peripheral portions of cotton pads are typically joined so that they are much stronger than central portions of the respective cotton pads. The inventors of the present invention have discovered that for this reason the cotton pad will further tend to be in much better condition when having been deformed to be pulled out of the dispenser.

Further, the user will not need to turn or tilt the dispenser from the upright position to determine where to position the fingers in relation to the withdrawal aperture; correct positioning of the fingers is clear from contemplating the side wall cut-out, which is visible from the side of the dispenser.

Dependent claims 4 to 5 define preferred embodiments of the first aspect of the invention. Specifically, with the embodiment of claim 5 it is ensured that the withdrawal aperture is not surrounded by any sharp edges or points, which might destroy the cotton pad when pulling it out of the dispenser. Further, with the embodiment of claim 5 the cut-outs are defined in such a way as to guide the thumb and the index finger, respectively, such that when gripping the bottommost cotton pad, the fingers are guided to grip a peripheral part of the cotton pad positioned centrally with respect to the withdrawal opening. This ensures that the cotton pad is easily withdrawn and that a smaller force is necessary to deform the cotton pad when withdrawing it, which again ensures that the surface structure of the cotton pad is not destroyed. With the embodiment of claim 5, it is ensured that the side wall, and thus the dispenser itself, can stand erect unaided with an appropriate side wall or material thickness.

In its second, third and fourth aspects the object of the invention is to provide a dispenser according to the introductory parts of claims 1 and 6, respectively, which may be manufactured in an easy and cheap way.

In the second and fourth aspects of the invention this object is met by means of a dispenser according to claim 1 and a method for its manufacture according to claim 8.

With dispensers of the type to which the present invention relates it is important that the shape of the side wall ensures that the stack of cotton pads to be positioned within the dispenser will be able to move downwards due to gravity. This is to ensure that it is always possible to withdraw the bottommost cotton pad from the dispenser. It would be natural to achieve this by making the shape of the side wall of the dispenser assume the form of a circular cylinder (if circular cotton pads are used). Further, it is important that the visual impression of the dispenser appeals to the end user. A circular-cylindrical shape of the side wall also fulfils this demand.

As would be known to the skilled person, it would be difficult and expensive to mould a cylinder-shaped side wall, e.g. by means of injection moulding. It would therefore be natural to make use of some other method of manufacturing the side wall, e.g. extruding it or folding and connecting two sides of a sheet of material. However, these methods of manufacture entail a number of drawbacks in relation to moulding of the dispenser. For example the methods would typically require substantial pre-treatment and after-treatment (e.g. cutting and joining), and the final result of products manufactured with such methods would typically not be as aesthetically appealing as products, which are e.g. injection moulded.

Now, according to claim 1 the side wall is moulded in a frusto-conical shape tapering towards the top end of the dispenser. This has been done in order to make it possible to remove the side wall from a mandrel after a moulding step, e.g. if the side wall has been manufactured by means of injection moulding. Further, the fewer steps typically related to injection moulding methods would make it cheaper to mould the product, especially in large quantities. The inventors of the present invention have surprisingly discovered that applying the frusto-conical shape of the side wall such that opposite parts of the side wall are inclined with respect to each other with an angle as low as 0.6° is enough to make it possible to remove the side wall from the mandrel by pulling it upwards when it has hardened after moulding. This corresponds to a draught angle of as low as 0.3°, as the above-mentioned angle between two opposite parts of the side wall correspond to two times the draught angle. The draught angle is defined as the angle between the longitudinal cylinder axis of the side wall and the side wall in a longitudinal cross section through the side wall. Further, the inventors have discovered that if the draught angle is below about 1°, to the human eye the shape of the side wall will appear as cylindrical. Best results are achieved with a draught angle between 0.3° and 0.8°, preferably 0.4° to 0.6°, and most preferred about 0.5°. Also, the slightly frusto-conical shape of the side wall further improves on the dispenser's ability to ensure that the cotton pads move downwards by means of gravity, without compromising the aesthetics of the dispenser.

Consequently, according to claim 8 the mandrel used for moulding the side wall has a corresponding frusto-conical shape tapering towards a top end of the mandrel, wherein opposite parts of the mandrel's sides are inclined with respect to each other with an angle between 0.6° and 2°, preferably between 0.8° and 1.5°, most preferred about 1°. In terms of draught angle, this corresponds to a draught angle of between 0.3° and 1°, preferably between 0.4° and 0.8°, most preferred about 0.5°.

Preferably, the side wall at the top end of the dispenser extends integrally into a top end wall so as to form a closed top end. In case such an integrally formed closed top end is provided, cotton pads are preferably stacked within the dispenser during manufacture of the dispenser and should be inserted before securing the end wall to the side wall.

If the dispenser further comprises cut-outs according to the dispenser as defined in claims 3 to 5, the cut-outs are preferably provided before securing the end wall to the side wall and before stacking the cotton pads within the volume defined by the side wall.

In the third aspect of the invention the latter object is met by means of a dispenser according to claim 6.

Accordingly, the collar wall of the bottom part extends from the end wall along an inner circumference of the supporting structure towards the bottom end of the dispenser. The bottom part therefore strengthens the supporting structure, which is the part of the dispenser exposed to the strongest forces during use. Following this, it is possible to make the side wall thinner and hereby provide a substantial reduction of the overall weight of the dispenser. Furthermore, attachment of the end wall to the side wall can be readily done by means of thermal joining such as plumbing or welding, preferably by means of at least two, more preferred at least three mutually spaced spot welds. Further, no inwards facing projections (which would be difficult and expensive to produce with injection moulding, cf. also above) or the like are needed to attach the end wall to the side wall. This also makes the dispenser more visually appealing, especially if manufactured from a transparent plastics material (as is preferred to make the contents visible).

Note that the dispenser according to the third aspect of the invention preferably is according to the first aspect of the invention, in which case the collar wall of the bottom part should be provided with a cut-out corresponding to and aligned with the cut-out of the side wall. Preferably, the dispenser according to the second aspect of the invention is according to the first aspect of the invention. Preferably, the dispenser according to the third aspect of the invention is according to the first and second aspects of the invention, in which case the collar wall of the bottom part should be provided with a cut-out corresponding to and aligned with the cut-out of the side wall.

BRIEF DESCRIPTION OF THE DRAWINGS

In the following the invention will be explained further with reference to the exemplary drawing, where like numbers refer to like features throughout the drawings, in which.

WRITTEN DESCRIPTION

Figure 1:
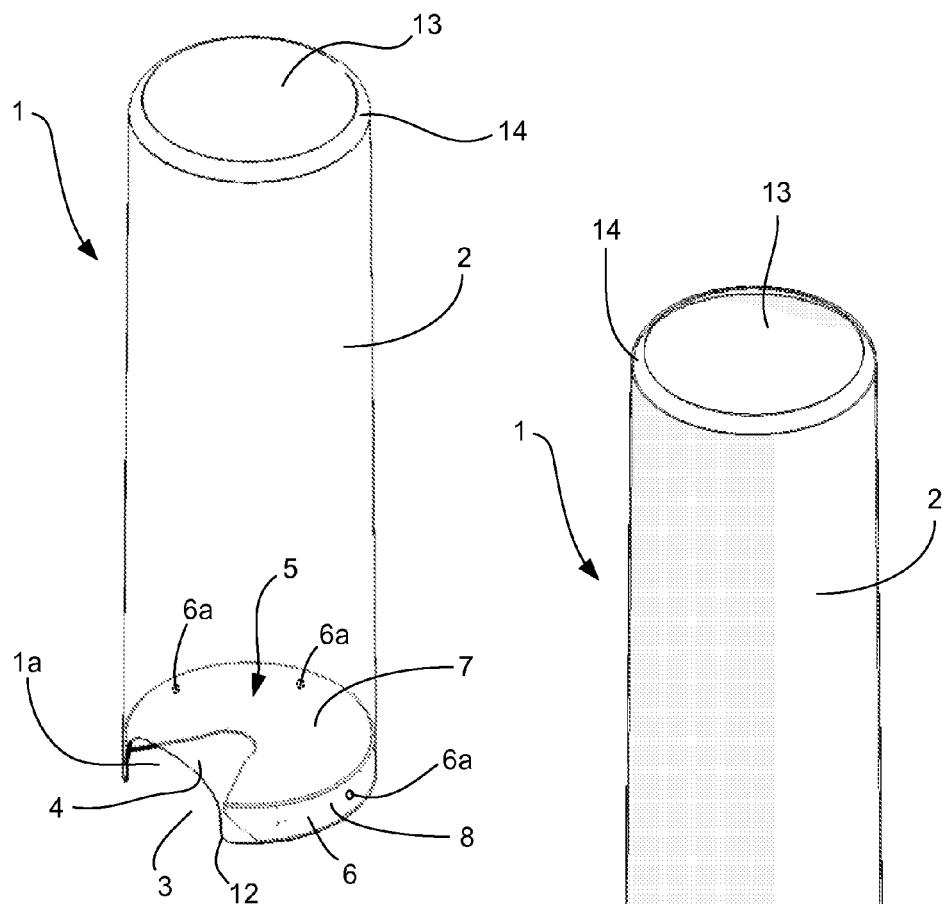
FIG. 1 shows a perspective view of an embodiment of a dispenser according to the first, second and third aspects of the present invention.
Figure 2:
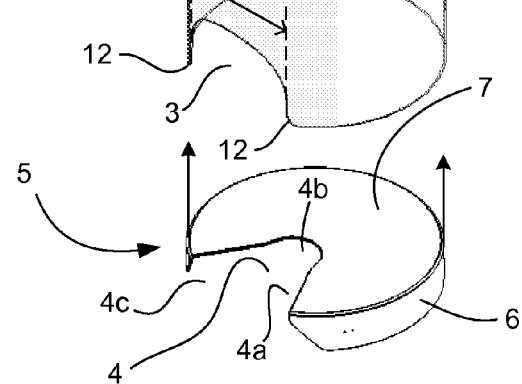
FIG. 2 shows an exploded perspective view of the dispenser of FIG. 1.
Figure 3:
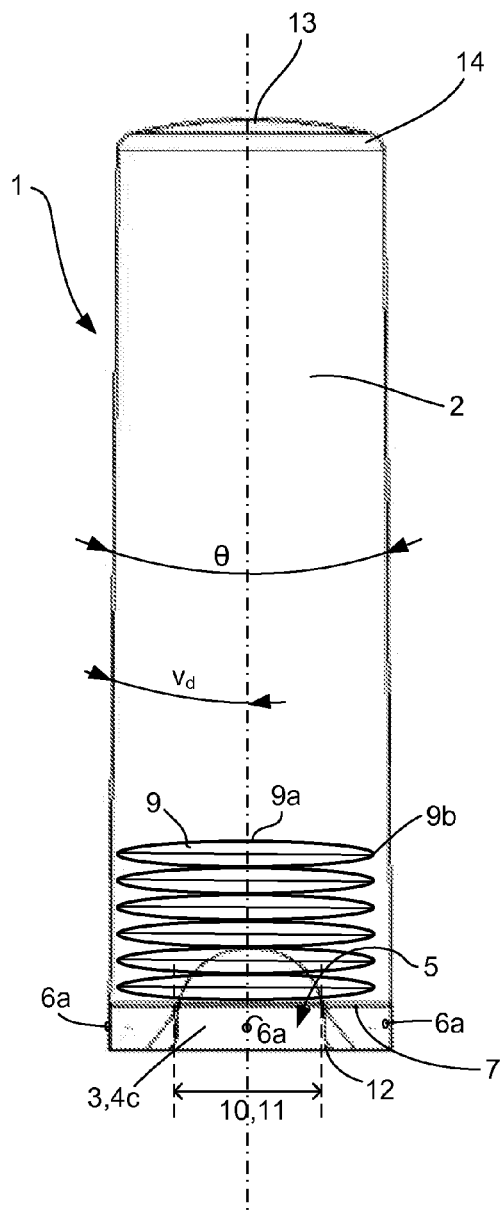
FIG. 3 shows a side view of the dispenser of FIG. 1, in which a number of cotton pads are stacked.

FIGS. 1 to 3 show different views of an embodiment of a dispenser 1 for dispensing cotton pads 9. It is understood that the term "cotton pads" also covers pads made partly of cotton or made entirely of other materials, such as paper pads, synthetic pads or pads made from a mix of paper and/or cotton and/or synthetic material. The dispenser 1 is made for disposable use and is made of a plastics material, preferably a transparent plastics material. Polypropylene PPH 12020, polypropylene PPC 13712 or PPC 13812, metocene HM648T, moplen EP548V or Adstif HA740R are preferred materials, but any suitable plastics material may be used.

The dispenser 1 comprises a top end and a bottom end (upwards and downwards, respectively, in FIGS. 1-3), a side wall 2 extending between the top and the bottom ends, and an end wall 7 near the bottom end. The side wall 2 and the end wall 7 of the dispenser define a volume adapted to accommodate a plurality of disc-shaped cotton pads 9 (only illustrated in FIG. 3) stacked with mutual flat surfaces 9a contacting each other.

The side wall 2 has a substantially tubular shape with a circular cross-section, the diameter of the side wall 2 generally being slightly larger than the diameter of the cotton pads 9. In this way disc-shaped cotton pads 9 can be arranged on top of each other inside the volume. It is understood that the cross section of the side wall may be of any shape suitable for accommodating a stack of the specific cotton pads to be withdrawn, such as oval, elliptical or polygonal. The dispenser may as well be used for accommodating rectangular cotton pads or for instance sanitary towels, panty-liners, nursing pads or other sanitary articles. Depending of the type of article, an oval, elliptical or polygonal cross section of the side wall may be particular expedient. The cross section of the side wall need not have the same shape as the cotton pads, sanitary towels, panty-liners, nursing pads or whatever sanitary article to be accommodated within the dispenser.

The side wall 2 has a substantially frusto-conical shape tapering towards the top end of the dispenser 1 with opposite parts of the side wall 2 inclined with respect to each other with an angle θ of about 1°, which corresponds to a draught angle $v_d$ of about 0.5°, as $\theta=2v_d$. The inside diameter of the thus substantially circular-cylindrical side wall 2 is preferably 2 to 7 cm, more preferred 4 to 5 cm everywhere in its length such as to accommodate the usual shape of a typical cotton pad. However, the diameter of course suitably varies slightly from the top to the bottom of the dispenser 1 according to the described inclination of said opposite parts of the side wall 2. In cases where the dispenser is to accommodate rectangular cotton pads or other articles, such as any of the sanitary articles mentioned above, the inside dimensions of the dispenser are selected so as to be suitable for accommodating the articles in question.

In the shown embodiment, the side wall 2 extends integrally into a top end wall 13 so as to form a closed top end. The top end wall 13 is slightly dome shaped, and a rounded transition 14 between the side wall 2 and top end wall 13 is provided. This configuration is particularly expedient, when the side wall 2, top end wall 13 and transition 14 are integrally shaped during injection moulding, cf. below, and this configuration ensures that the moulded product can easily let go of the mandrel after moulding. Other shapes and combinations of the top end wall and transition are conceivable, such as for instance a substantially plane top end wall and a chamfered transition.

As is best seen from FIGS. 1 and 3, at the bottom end, the side wall 2 extends beyond the end wall 7 such as to form a supporting structure 8 for supporting the dispenser 1 in an upright position. This prevents the bottommost cotton pad of the dispenser 1 from coming into contact with especially moist, but also with soil from the surface (not shown) on which the dispenser 1 is positioned.

A first cut-out 3 provided in the side wall 2 extends upwards from the bottom end of the dispenser 1 so as to form an entrance into the volume through the side wall 2, and a second cut-out 4 provided in the end wall 7 extends from the cut-out 3 such that the cut-outs 3, 4 comprise a mutual transition to form one combined withdrawal aperture 1a. The withdrawal aperture 1a is arranged such as to enable withdrawal of the bottommost cotton pad by gripping a peripheral portion 9b of the cotton pad with an indexing finger of a hand, the indexing finger preferably being inserted at the cut-out 4, and a thumb of the hand, the thumb preferably being inserted at the cut-out 3, and pulling the cotton pad out of the withdrawal aperture 1a by means of deformation of the cotton pad. Preferably, the cut-out 3 is thus of a size that allows a thumb of a hand to be inserted into the dispenser 1. This way of inserting the fingers is expedient, when the dispenser 1 is placed on for instance a table or the like, and the user is standing up. In this way it is possible to withdraw a cotton pad without lifting the dispenser 1 from the table. Inserting, for instance, the thumb of a hand at the cut-out 4 and the indexing finger at the cut-out 3 in order to withdraw the bottommost cotton pad is also conceivable. For this reason, also the cut-out 4 is preferably of a size that allows the thumb to be inserted. This way of inserting the fingers may be particularly expedient, when the dispenser 1 is in a more elevated position in relation to the user, like for instance on a shelf.

The cut-out 3 has a general arc shape, more specifically a substantially semicircular shape. The general arc shape of the cut-out 3 assists in guiding the finger inserted through the cut-out 3 towards a peripheral portion 9b of the bottommost cotton pad so as to enable a good grip before withdrawing the cotton pad. It is understood that the cut-out 3 may nevertheless be of a different shape, such as for instance generally rectangular or polygonal. The cut-out 3 furthermore has rounded corners 12 at its bottom, such that when a cotton pad is withdrawn it will not be torn or otherwise damaged by sharp corners. Multiple cut-outs 3, such as two, three or more, extending upwards from the bottom end of the dispenser may be provided in the side wall so that the sections of side wall in between the cut-outs serve as legs. Preferably, the multiple cut-outs are evenly distributed along the circumference of the side wall so as to provide a reliable support for the dispenser. Preferably, in cases where multiple cut-outs 3 are provided in the side wall extending upwards from the bottom end of the dispenser, a corresponding number of cut-outs 4 are provided in the end wall so that multiple withdrawal apertures are thus formed. Alternatively, legs may be provided as sections of the side wall projecting beyond the end wall. The cut-out 4 extends in the end wall 7 from the side wall 2 in a tapering, preferably substantially triangular shape 4a to a substantially circular and centrally placed shape 4b such as to form a keyhole-like shape. The shape of the cut-out 4 follows a smooth pattern such that when a cotton pad is withdrawn, it will not be damaged. This keyhole-like shape assists in guiding the finger inserted through the cut-out 4 in a manner and with the purpose as described above in relation to the cut-out 3. However, it is understood that the second cut-out may be of a different shape, such as for instance generally rectangular, elliptical, oval, generally arc shaped or polygonal.

As is best seen in FIG. 2, the end wall 7 forms part of a bottom part 5. The bottom part 5 is formed separately from the side wall 2. The bottom part 5 comprises the end wall 7 and a circumferential collar wall 6, the collar wall 6 extending from a periphery of the end wall 7. In a mounted position of the bottom part 5 (as shown in FIGS. 1 and 3), the collar wall 6 further extends along an inner circumference of the supporting structure 8 towards the bottom end of the dispenser 1 and is attached to an inner surface of said inner circumference. The collar wall 6 is attached to the side wall 2 by thermal joining in the form of two, three, or more than three mutually spaced spot welds 6a. Alternatively, the weld is one continuous, circular-shaped weld seem. It is understood that the weld seem follows the side wall, so that, if the side wall has a cross section of another shape than circular, the shape of the continuous weld seem will follow the cross sectional shape of the side wall and form for instance a polygonal, oval or elliptical weld seem. In this way, manufacturing of the dispenser 1 is made easier as the collar wall 6 of the bottom part 5 can easily be attached to the side wall 2. Other ways of attaching the collar wall 6 can be used; for example, the collar wall 6 may be attached to the side wall by snap fit engagement, friction fit, rabbeting or adhesion.

Figure 4:
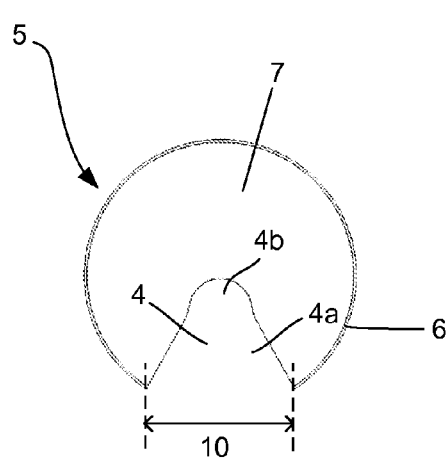
FIG. 4 shows a bottom view of a bottom part of the dispenser of FIG. 1.
Figure 5:
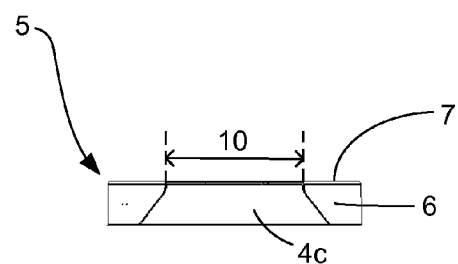
FIG. 5 shows a side view of the bottom part of FIG. 4.

FIGS. 4 and 5 show the bottom part 5 of the dispenser 1. When the bottom part 5 is arranged within the side wall 2, a width 10 of the cut-out 4 at the mutual transition between the cut-outs 3, 4 is substantially equal to the corresponding width 11 of the cut-out 3 at the mutual transition, such that the cut-out 4 at the mutual transition flushes with the cut-out 3.

The cut-out 4 in the end wall 7 extends further into the collar wall 6. The cut-out 4 extends such that the collar wall 6 has an opening 4c tapering from the bottommost part of the collar wall 6 up to the end wall 7. This is advantageous as, in a mounted state, the collar wall 6 will not appear through the cut-out 3 in the side wall 2, and access for a user's finger to the cut-out 4 in the end wall 7 is enabled. Preferably, in case where multiple cut-outs 3 are provided in the side wall extending upwards from the bottom end of the dispenser, a corresponding number of openings 4c are provided in the collar wall so that it will not appear through the cut-outs in the side wall. The sections of side wall and collar wall in between the cut-outs and openings, respectively, will serve as supporting legs for the dispenser. Preferably, the multiple cut-outs and openings are evenly distributed along the circumference of the side wall and collar wall, respectively, so as to provide a reliable support for the dispenser.

In the following, a method for manufacturing an embodiment of the dispenser 1 is explained. First, a mandrel (not shown) with a frusto-conical shape tapering towards a top end of the mandrel is provided. Opposite parts of the mandrel's sides are inclined with respect to each other with an angle θ of about 1°, which results in a draught angle $v_d$ of about 0.5°. The side wall 2 of the dispenser 1 is then injection moulded by use of the mandrel. Hereby the side wall 2 obtains a corresponding frusto-conical shape tapering towards the top end of the dispenser 1, where opposite parts of the side wall 2 are inclined with respect to each other with an angle θ of about 1° corresponding to a draught angle $v_d$ of 0.5°. After hardening, the moulded side wall 2 is removed from the mandrel in the direction in which the mandrel tapers. The removal is eased due to the inclination of the side wall 2 and the mandrel.

In the shown embodiment of the dispenser 1, a closed top end is provided by injection moulding integrally with the side wall 2 a top end wall 13. The top end wall 13 is slightly dome-shaped, and a rounded transition 14 between the side wall 2 and top end wall 13 is provided. As explained above, this configuration is particularly expedient as it ensures that the moulded product can easily let go of the mandrel after moulding.

The bottom part 5 is also manufactured by injection moulding. Preferably, opposite parts of the collar wall 6 of the bottom part 5 are inclined with respect to each other with an angle θ corresponding to that of the side wall 2. This eases removal of the bottom part from mould after moulding and ensures a better attachment of the collar wall 6 to the inner surface of the inner circumference of the side wall 2, cf. below. However, other ways of manufacturing the bottom part are conceivable depending on, for instance, the specific choice of material for the bottom part.

The cut-outs 3, 4 of the side wall 2 and the end wall 7, respectively, and the cut-out 4c in the collar wall 6 are provided during moulding by means of one or more cores or inserts in the respective moulds. Alternatively, the cut-outs may be provided after moulding by actually cutting them out of the side wall, end wall and collar wall, respectively. Providing the cut-outs 3, 4 and 4c before filling the dispenser 1 with cotton pads (as will be described below) and securing the bottom part 5 to the side wall 2 (as will also be described below), is expedient.

A stack of disc-shaped cotton pads 9 is then inserted into the volume of the dispenser 1 from its bottom end so that mutual flat surfaces 9a of the cotton pads 9 are contacting each other. The closed top end of the dispenser 1 prevents the cotton pads 9 from falling out of the dispenser 1 during the remaining manufacturing steps.

The bottom part 5 is now inserted in the dispenser 1 from the bottom end of the latter. In the mounted state of the bottom part 5, the collar wall 6 extends from the end wall 7 towards the bottom end of the dispenser 1 in order to ease fastening and providing strength to the supporting structure 8. Also, in this way, edges (i.e. the bottom edge of the collar wall 6), which could otherwise damage the cotton pads, are avoided inside the volume of the dispenser 1. The bottom part 5 is fastened to the side wall 2 by means of thermal joining in the form of three mutually spaced spot welds 6a between an inner surface of the side wall 2 and an outer surface of the collar wall 6. It is understood that the collar wall could as well be attached to the side wall by two or more than three mutually spaced spot welds or by one continuous weld seem having a shape following the cross sectional shape of the side wall, i.e. for instance circular, oval, elliptical or polygonal.

The bottom part 5 is positioned in relation to the side wall 2 so that the end wall 7 is at a distance of about 1 cm from the bottom end. The height of the collar wall 6 is also about 1 cm so that, in a mounted condition of the bottom part 5, the side wall 2's and the collar wall 6's respective end edges substantially flush. It is understood, however, that the collar wall 6 may be of a height smaller or larger than the distance between the end wall 7 and the bottom end of the side wall 2 in a mounted condition of the bottom part. Said distance may of course also assume other dimensions than 1 cm, for instance 2 cm.

The side wall 2, top end wall 13 and transition 14 are thus preferably moulded in one piece, and in all aspects and embodiments preferably have a wall or material thickness of 0.4 to 2 mm, more preferred 0.5 to 0.8 mm and most preferred 0.6 mm. The wall thickness should be as small as possible to save material and reduce weight, but should be large enough to provide sufficient strength so as to enable the dispenser to stand erect unaided.

The side wall 2, top end wall 13 and transition 14 are preferably manufactured from polypropylene, preferably a harder variant (i.e., with a high tensile modulus after hardening), yet still with a good ability to flow during moulding (i.e. with a high melt flow index). A tensile modulus (according to ISO 527-2) of between 1000 MPa and 3000 MPa, preferably between 1500 MPa and 2200 MPa and more preferably of around 1800 MPa and/or a melt flow index (230°/2.16 kg; according to ISO 1133) of between 50 g/10 min and 120 g/10 min, preferably between 60 g/10 min and 110 g/10 min and more preferably of around 100 g/10 min are suitable. Polypropylene PPH 12020, polypropylene PPC 13712 or PPC 13812, Metocene HM648T, Moplen EP548V or Adstif HA740R are preferred materials, but any suitable plastics material may be used.

The height of the side wall 2, and hereby of the entire dispenser 1, is preferably 10 to 35 cm, more preferred 15 to 25 cm. This allows for a suitable number of cotton pads to be stored within the dispenser 1. A dispenser of a smaller size suitable for travel is envisaged. The height of the side wall of the dispenser suitable for travel is preferably 3 cm to 10 cm, more preferred 5 cm to 8 cm. Also, a dispenser of a larger size suitable for a large-scale consumer is envisaged. The height of the side wall of the dispenser suitable for a large-scale consumer is preferably 25 cm to 40 cm, more preferred 30 cm to 35 cm. During integral injection moulding of the side wall 2, top end wall 13 and transition 14, the moulding material is typically introduced at or near a center of the top end wall 13 from which it extends or is dispersed to the transition 14 and further to the side wall 2 until it reaches the bottom end of the latter. Polypropylene has the advantage of having relatively low viscosity, for example compared to polycarbonate, which ensures that the material is satisfactorily dispersed even with side walls of greater height and smaller thickness. With a height of the dispenser of about 20 cm and using a suitable polypropylene it is possible to successfully injection mould a relatively hard dispenser 1 as described, which has a low wall thickness, i.e., a wall thickness as low as 0.5 or 0.6 mm. With dispensers of smaller height, even lower wall thicknesses are preferable.

Due to ease of manufacture the wall thickness of the bottom part 5 is typically similar to that of the above-described parts. However, to improve stability of the dispenser 1, in some instances it may be preferred to provide it with a larger wall thickness. However, since the bottom part has typically smaller dimensions than the integrally shaped side wall 2, top end wall 13 and transition 14, and improved stability of the dispenser 1 is often not an issue, it is preferred that the wall thickness of the bottom part 5 is somewhat smaller, preferably 0.2 to 1 mm, more preferred 0.3 to 0.5 mm.

It is understood that the invention is not limited to the embodiments shown in the figures and described in the above, but variations and modifications may be carried out without departing from the scope of the appended claims. For example, a closed top end need not be integrally formed with the side wall. A closed top end may, for instance, be provided by means of a top lid fastened to the side walls by means of screw thread, friction fit or snap lock engagement. Alternatively, the side wall may form a closed top end itself by tapering into a flat closed top end. The flat top end may be closed by means of a welded or glued seam. Further, the end wall could be formed integrally with the side wall, and the end wall could be positioned at the bottom of the side wall instead of being raised from the latter. Also, the side wall, top end wall and/or transition could instead of being manufactured integrally be moulded or manufactured in several separate parts that are later assembled.

The invention claimed is:

1. A dispenser for dispensing cotton pads the dispenser comprising
   a top end and a bottom end,
   a side wall extending between the top and the bottom ends, and
   an end wall near the bottom end,
   the side wall and the end wall defining a volume adapted to accommodate a plurality of disc-shaped cotton pads stacked with mutual flat surfaces contacting each other, wherein
   the side wall is moulded in a frusto-conical shape tapering towards the top end of the dispenser, wherein opposite parts of the side wall are inclined with respect to each other with an angle ($\theta$) between 0.6° and 2°.

2. A dispenser according to claim 1, wherein the side wall is moulded of a plastics material with a melt flow index (230°/2.16 kg) of between 50 g/10 min and 120 g/10 min.

3. A method for producing a dispenser according to claim 1, the method comprising the steps of:
   providing a mandrel with a frusto-conical shape tapering towards a top end of the mandrel, wherein opposite parts of the mandrel's sides are inclined with respect to each other with an angle between 0.6° and 2°,
   moulding the side wall on the mandrel,
   removing the side wall from the mandrel in a direction in which the mandrel tapers, and
   providing the end wall and inserting it from the bottom end of the dispenser into the volume defined by the side wall, and securing it to the side wall.

4. A method according to claim 3, wherein the side wall is moulded from a plastics material with a tensile modulus of between 1000 MPa and 3000 MPa.

5. A method according to claim 3, wherein the dispenser further comprises:
   a top end and a bottom end,
   a side wall extending between the top and the bottom ends,
   an end wall near the bottom end, and
   a bottom part formed separately from the side wall, the bottom part comprising the end wall and a circumferential collar wall, the collar wall extending from a periphery of the end wall along at least part of an inner circumference of the supporting structure towards the bottom end of the dispenser and being attached to an inner surface of said inner circumference,
   wherein the side wall and the end wall define a volume adapted to accommodate a plurality of disc-shaped cotton pads stacked with mutual flat surfaces contacting each other,
   wherein a first cut-out provided in said side wall extends upwards from the bottom end of the dispenser so as to form an entrance into said volume through the side wall,
   wherein a second cut-out provided in said end wall extends from the first cut-out such that the cut-outs comprise a mutual transition to form one combined withdrawal aperture,
   wherein the withdrawal aperture is arranged such as to enable withdrawal of a bottommost cotton pad in said volume by gripping a peripheral portion of the cotton pad with an indexing finger of a hand, the indexing finger being inserted at the second cut-out, and a thumb of the hand, the thumb being inserted at the first cut-out, and pulling the cotton pad out of the withdrawal aperture by means of deformation of the cotton pad,
   wherein the first cut-out extends from said bottom end of the dispenser in a general arc shape,
   wherein the side wall at the bottom end extends beyond the end wall such as to form a supporting structure for supporting the dispenser in an upright position, the end wall being placed at a distance from the bottom end of the dispenser between 0.2 cm and 5 cm, and
   wherein the cut-outs of the side wall and the end wall and provided before securing the end wall to the side wall.

6. A method according to claim 3, the method comprising the step of stacking a plurality of cotton pads within a volume defined by the side wall with mutual flat surfaces contacting each other, the side wall at the top and extending integrally into a top end wall so as to form a closed top end.

7. A method according to claim 3, wherein the side wall is mounded from a plastics material with a melt flow index (230°/2.16 kg) of between 50 g/10 min and 120 g/10 min.

8. A dispenser according to claim 1, wherein the side wall at the bottom end extends beyond the end wall such as to form a supporting structure for supporting the dispenser in an upright position.

9. A dispenser for dispensing cotton pads, the dispenser comprising
   a top end and a bottom end,
   a side wall extending between the top and the bottom ends, and
   an end wall near the bottom end,
   the side wall and the end wall defining a volume adapted to accommodate a plurality of disc-shaped cotton pads stacked with mutual flat surfaces contacting each other, wherein
   a first cut-out provided in said side wall extends upwards from the bottom end of the dispenser so as to form an entrance into said volume through the side wall, and
   a second cut-out provided in said end wall extends from the first cut-out such that the cut-outs comprise a mutual transition to form one combined withdrawal aperture,
   the withdrawal aperture being arranged such as to enable withdrawal of a bottommost cotton pad in said volume by gripping a peripheral portion of the cotton pad with an indexing finger of a hand, the indexing finger being inserted at the second cut-out, and a thumb of the hand, the thumb being inserted at the first cut-out, and pulling the cotton pad out of the withdrawal aperture by means of deformation of the cotton pad, the first cut-out extending from said bottom end of the dispenser in a general arc shape, the side wall at the bottom end extending beyond the end wall such as to form a supporting structure for supporting the dispenser in an upright position.

10. A dispenser according to claim 9, further comprising a plurality of disc-shaped cotton pads stacked within the volume with mutual flat surfaces contacting each other, the side wall and the cotton pads being provided such that when the dispenser is placed in the upright position, the remaining stack of cotton pads will move downwards by means of gravity when the bottommost cotton pad is withdrawn through the withdrawal aperture.

11. A dispenser according to claim 10, wherein
a width of the second cut-out at said mutual transition is larger or substantially equal to a corresponding width of the first cut-out at said mutual transition, such that the second cut-out at said mutual transition flushes with or extends to a distance from an edge of the first cut-out.

12. A dispenser according to claim 10, wherein the second cut-out extends from the side wall in a tapering shape to a substantially circular and centrally placed shape such as to form a keyhole-like shape.

13. A dispenser according to claim 10, wherein the side wall is made of a plastic material with a tensile modulus of between 1000 MPa and 3000 MPa.

14. A dispenser for dispensing cotton pads according to claim 9, wherein the dispenser
further comprises a bottom part formed separately from the side wall, the bottom part comprising the end wall and a circumferential collar wall, the collar wall extending from a periphery of the end wall along at least part of an inner circumference of the supporting structure towards the bottom end of the dispenser and being attached to an inner surface of said inner circumference.

15. A dispenser according to claim 14, wherein the collar wall is attached to the side wall by thermal joining such as plumbing or welding.

16. A dispenser according to claim 9, wherein
a width of the second cut-out at said mutual transition is larger or substantially equal to a corresponding width of the first cut-out at said mutual transition, such that the second cut-out at said mutual transition flushes with or extends to a distance from an edge of the first cut-out.

17. A dispenser according to claim 9, wherein the second cut-out extends from the side wall in a tapering shape to a substantially circular and centrally placed shape such as to form a keyhole-like shape.

18. A dispenser according to claim 9, wherein the side wall is made of a plastics material with a tensile modulus of between 1000 MPa and 3000 MPa.

* * * * *